US008357675B2

(12) United States Patent
Ashcroft et al.

(10) Patent No.: US 8,357,675 B2
(45) Date of Patent: Jan. 22, 2013

(54) 17-ALPHA-SUBSTITUTED DERIVATIVES OF ESTRADIOL WITH WOUND-HEALING ACTIVITY

(75) Inventors: Gillian Ashcroft, Manchester (GB); Mario Brufani, Castelgandolfo (IT); Francesca Ceccacci, Rome (IT); Paolo Maria Farina, Milan (IT); Luigi Filocamo, Rome (IT); Barbara Garofalo, Rome (IT); Roberta Joudioux, Rome (IT); Adriana Maggi, Milan (IT); Rinaldo Marini Bettolo, Rome (IT); Luisa Maria Migneco, Rome (IT)

(73) Assignee: Euticals S.p.A. (IT)

( * ) Notice: Subject to any disclaimer, the term of this patent is extended or adjusted under 35 U.S.C. 154(b) by 674 days.

(21) Appl. No.: 11/989,807

(22) PCT Filed: Jul. 28, 2006

(86) PCT No.: PCT/EP2006/007488
§ 371 (c)(1),
(2), (4) Date: Oct. 22, 2009

(87) PCT Pub. No.: WO2007/014711
PCT Pub. Date: Feb. 8, 2007

(65) Prior Publication Data
US 2010/0035796 A1    Feb. 11, 2010

(30) Foreign Application Priority Data

Aug. 2, 2005 (IT) .................................. MI05A1516

(51) Int. Cl.
*A61K 31/567* (2006.01)
*C07J 1/00* (2006.01)

(52) U.S. Cl. ........................................ 514/182; 552/631
(58) Field of Classification Search .................. 552/630, 552/631; 514/182
See application file for complete search history.

(56) References Cited

FOREIGN PATENT DOCUMENTS
WO    WO-98/03180 A2    1/1998

OTHER PUBLICATIONS

Morales et al., "Estrogen Promotes Angiogenic Activity in Human Umbilical Vein Endothelial Cells In Vitro and in a Murine Model", Circulation, America Heart Association, vol. 91, No. 3 pp. 755-763, Dallas, TX., Feb. 1, 1995.
El Garrouj et al., "Steroidal Affinity Labels of the Estrogen Receptor 1. 17α(Bromoacetoxy)Alkyl/alkynylestradiols", Journal of Medicinal Chemistry, American Society, vol. 36, No. 20, pp. 2973-2983, Washington, 1993.
Kasiotis et al., "High Affinity 17α-substituted estradiol derivatives: Synthesis and evaluation of estrogen receptor agonist activity", Steroids, Elsevier Science Publishers, vol. 71, No. 3, pp. 249-255, New York, NY, Mar. 2006.

*Primary Examiner* — Barbara P Badio
(74) *Attorney, Agent, or Firm* — Lerner, David, Littenberg, Krumholz & Mentlik, LLP

(57) ABSTRACT

The invention relates to 17α-(5-hydroxy-$C_5$-hydrocarbyl)-1,3,5(10)-estratrien-3,17β-diol derivatives having cicatrising activity, preferably for topical use on wounds, without significant systemic effects, and to pharmaceutical compositions containing them. In particular, the invention relates to estradiol 17α-(5-hydroxypentyn-1-yl)derivatives and 3-esters, 5'-esters and 3,5'-diesters thereof and to a process for the preparation thereof by reaction of 3-OR-protected estrone with an alkali metal derivative of OR-protected 5-pentynol, followed by 3-, 5'- or 3,5'-esterification.

19 Claims, No Drawings

17-ALPHA-SUBSTITUTED DERIVATIVES OF ESTRADIOL WITH WOUND-HEALING ACTIVITY

FIELD OF INVENTION

This invention relates to new 17α-substituted estradiol derivatives with a wound-healing action. In particular, the invention relates to estradiol, or a 3-ether or 3-ester thereof, substituted at its 17α position with a 5-hydroxy-pentyl, -penten-1-yl or pentin-1-yl group, possibly esterified, which is useful for the preparation of medicinal products designed to promote wound-healing.

BACKGROUND TO THE INVENTION

It is known from G. S. Ashcroft et al., 1997; Nat. Med. 3(11) 1209-15 (Ashcroft et al. 1997) that estrogens accelerate the healing of wounds associated with an increase in the levels of transforming growth factor-β (TGF-β). G. S. Ashcroft et al., Am. J. Patholo. 1999; 155, 1137-1146 (Ashcroft et al. 1999) also observed that the wound-healing process slows with age, and that the wound-healing time decreases after the application of topical estrogens.

Wound-healing comprises three overlapping stages: inflammation, tissue formation and tissue modelling. This comprises a series of events involving cytokines secreted by platelets, macrophages, neutrophils, fibroblasts and epidermal cells on which the estrogens can act to promote wound-healing (Y. M. Bello et al. JAMA, 2000; 283, 716-718). In particular, a marked reduction in transforming growth factor-β (TGF-β) has been observed in elderly women compared with the levels found in the wounds of young women.

A review of the action of estrogens on the skin, published by M. G. Shah et al. in Am. J. Clin. Dermatol. 2001; 2(3): 143-50, describes the topical use of 0.01% estradiol and 0.3% estriol.

Experimental biochemical and pharmacological animal models confirm that estrogens promote the repair of damaged skin. In particular, it has been proved that cultured fibroblasts from the dermis of elderly women secrete a smaller amount of TGF-$β_1$ than the fibroblasts of young women, and that the addition of estrogens to the fibroblast cultures increases the amount of TGF-β produced to the same level in the fibroblasts of both young and elderly women.

G. J. Gendimenico et al., in Arch. Dermatol. Research; (2002): 294(5), 231-6, demonstrated that both 17α-estradiol and 17β-estradiol repair the sun-damaged skin of hairless mice.

G. S. Ashcroft et al., in J. Clin. Investigation (2003), 111, 1309-18 (Ashcroft et al. 2003a), published the results of in vivo wound-healing experiments in mice lacking the MIF (Macrophage migration Inhibitory Factor) gene, which demonstrated that excessive inflammation and the phenotype associated with estrogen reduction are reversed in the absence of MIF, and the results of parallel in vitro experiments, which demonstrated a major reduction in estrogen-mediated MIF production by activated murine macrophages.

Finally, G. S. Ashcroft et al., in Am. J. Clin. Dermatol. (2003), 4(11), 737-43 (Ashcroft et al. 2003b), described the potential role of the estrogens in wound-healing.

All these data indicate that estrogens are an important hormonal control factor in the production and secretion of growth factor TGF-β by the dermal fibroblasts.

Estradiol (17beta-estradiol) and estriol, used topically, promote wound-healing (Ashcroft et al. 2003b).

However, estradiol possesses systemic estrogenic activity, even if administered on the skin, so the product is also administered by that route using therapeutic transdermal systems (TTS). A study of the permeation, penetration and metabolism of estradiol administered by the cutaneous route was recently published by A. Mahmud et al. in Skin Pharmacol. Physiol. (2005), 18(1) (Mahmud et al. 2005). Estriol is much less active than estradiol, but must be used at concentrations 30 times greater in order to be effective, as described in Shah et al. 2001.

As an impediment to wound-healing in elderly people poses a huge problem in terms of costs, morbidity and mortality, as stated in Ashcroft et al. 2003b, it is important to provide new estrogenic agents able to accelerate the wound-healing process, which can be used when such acceleration is useful for therapeutic purposes, and have a low systemic activity potential.

PRIOR ART

U.S. Pat. No. 3,265,718, which is incorporated herein in its entirety as reference, describes aromatic steroids substituted at the 17α-position with a 3-hydroxy-1-propinyl or 3-hydroxy-1-propenyl group, optionally esterified. A cholesterol-reducing activity predominating over the estrogenic activity is indicated for these compounds.

U.S. Pat. No. 3,303,205, also incorporated herein in its entirety as reference, discloses a process for the introduction of a hydroxyalkyl group containing at least three linear carbon atoms at the 17α position of a steroid, to obtain spiro derivatives at the 17-steroid position. For this reason, said document only describes 17α-(3-hydroxypropyl-) and 17α-(4-hydroxybutyl-) steroid derivatives, including estradiol.

R. P. Boivin et al. (J. Med. Chem. 2000, 43, 4465-78) disclose 17α-(3-hydroxypropin-1-yl)estradiol and 17α-(3-bromopropin-1-yl)estradiol due to their inhibitory effect on steroid sulphatase, which is high in the case of the 3-bromo derivative, and very low in the case of the 3-hydroxy derivative.

El Garrouj et al. (J. Med. Chem. 1993, 36, 2973-83) disclose 17α-(4-hydroxybutin-1-yl)estradiol and 17α-(8-hydroxyoctin-1-yl)estradiol as intermediates in the preparation of markers for the estrogen receptor, these markers being their 4' and 8' bromoacetates.

Estradiol derivatives substituted at the 17α-position with a ω-hydroxlylated hydrocarbon containing 5 carbon atoms are not described in the literature.

SUMMARY OF THE INVENTION

It has now been found that estradiol derivatives substituted at the 17α-position with an ω-hydroxylated hydrocarbon containing 5 carbon atoms and the ω-esters thereof have excellent wound-healing activity. In particular, it has been observed that 17α-(5-acetoxypentin-1-yl)-1,3,5(10)-estratriene-3,17β-diol has a marked effect on the wound-healing process.

It has also been found that the wound-healing effect can be observed through all the parameters which predict a wound-healing activity, such as reduction of the wound area, reduction of the macrophages in the wound area, and reduction of all the inflammation parameters, especially MIF and TGF-β.

Finally, it has been found that estradiol derivatives substituted at the 17α-position with an ω-hydroxylated hydrocarbon containing 5 carbon atoms and the ω-esters thereof are practically devoid of systemic estrogenic activity, or that such activity is so low that it does not carry a potential risk of estrogenic or feminising side effects.

In the following, estradiol derivatives substituted at the 17α position with an ω-hydroxylated hydrocarbon containing 5 carbon atoms and the ω-esters of said derivatives will be referred to as "estradiol 17α-C5-hydroxyhydrocarbyl derivatives".

The term "lower alkyl", referred to as "Alk", is a straight or branched alkyl group containing 1 to 4 carbon atoms, in particular methyl ("Me") or ethyl ("Et").

The term "lower alkoxy" is an AlkO group, in particular MeO or EtO, as defined above.

The term "lower alkanoyl" is the acyl moiety of a straight or branched monocarboxylic acid containing 1 to 5 carbon atoms, such as formyl, acetyl, propionyl, butanoyl, valeroyl, pivaloyl.

The term "acyl", referred to as "Ac", is the acyl moiety from an unsaturated monocarboxylic acid containing 3 to 5 carbon atoms, the acyl moiety of a monocarboxylic acid containing 1 to 5 carbon atoms, said acyl moieties being optionally substituted with a group selected from carboxy, methoxycarbonyl, ethoxycarbonyl, phenyl, tolyl, xylyl, methoxyphenyl, fluorophenyl, chlorophenyl, bromophenyl, nitrophenyl, dimethoxyphenyl, 1-naphthyl, 2-naphthyl, pyridyl, C3-7 cycloalkyl, or an acyl moiety from a haloalkanoic acid containing 2 to 5 carbon atoms.

DETAILED DISCLOSURE

According to an aspect, the present invention relates to novel estradiol derivatives substituted at the 17α-position with an ω-hydroxylated hydrocarbon containing 5 carbon atoms and to their ω-esters, of formula I

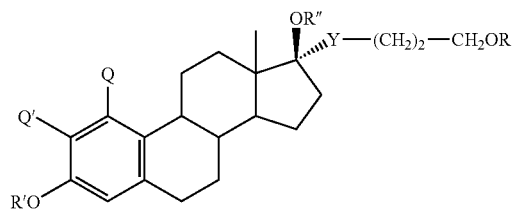

in which Q is hydrogen or methyl, Q' is hydrogen, methyl or lower alkoxy, R is hydrogen or acyl, R' is hydrogen, lower alkanoyl or a R' group which is a lower alkyl or ($C_5$-$C_6$) cycloalkyl group and R" is hydrogen or a lower alkanoyl group, Y is an ethylene group (—$CH_2$—$CH_2$—), an ethenylene group (—CH=CH—) or an ethynylene group (—C≡C—) and in which double bonds can also be present at the 6-position, at the 8-position, at the 9(11)-position or at the 6- and 8-steroid positions.

The compounds of formula I, optionally $\Delta^6$, $\Delta^8$, $\Delta^{9(11)}$ or $\Delta^{6,8}$, in which Y is ethynylene, can be prepared as disclosed in U.S. Pat. No. 3,265,718, using n-pent-1-yn-5-ol (herein referred to as "5-pentynol") in place of propargyl alcohol, by treating a 17-oxo derivative of formula II

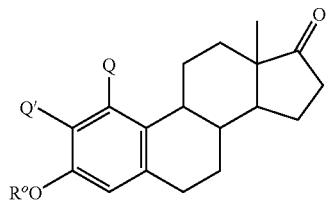

optionally $\Delta^6$, $\Delta^8$, $\Delta^{9(11)}$ or $\Delta^{6,8}$, in which R° is hydrogen, a protecting group P° stable to alkaline conditions or the R'a group, with the alkali metal derivative of the 5-pentynol derivative, of formula III

in which R is as defined above, and hydrolising the reaction mixture.

The reaction between the 17-oxosteroid and the alkali metal derivative of compound III is carried out at room temperature in an anhydrous inert solvent.

Typically, the derivative of compound III, in which R is H or an alkali-stable protecting group, with an alkali metal, preferably lithium, sodium or potassium, is prepared in situ from 5-pentynol with the selected metal or a derivative thereof, e.g. with ammonia or a hydrocarbon, such as sodium amide, potassium amide or butyllithium, in an anhydrous solvent.

The starting compounds of formula II, optionally $\Delta^6$, $\Delta^8$, $\Delta^{9(11)}$ or $\Delta^{6,8}$, are disclosed in U.S. Pat. No. 3,265,718 or can be prepared according to methods well known to those skilled in the art. In particular, the preparation of the compounds of formula II in which R' is a protecting group P° can be carried out according to one of the methods described by T. W. Greene et al. in "Protecting groups in Organic Synthesis, $3^{rd}$ Edition, J. Wiley & Sons, 1999" pages 249-276. Preferred protecting groups are 2-tetrahydropyranyl and t-butyldimethylsilyl. Estrone tetrahydropyranyl ether is disclosed in J. Org. Chem. 1979, 44, 1438 and estrone t-butyldimethylsilyl ether is disclosed in J. Am. Chem. Soc. 1972, 94, 6190. The corresponding ethers of $\Delta^6$, $\Delta^8$, $\Delta^{9(11)}$ estrone, of $\Delta^{6,8}$ estrone (equilenin) and of their derivatives are prepared analogously.

The alkali-stable protecting group, such as 2-tetrahydropyranyl or a silylating group, in particular a $Si(Alk)_3$ group, in which Alk is lower alkyl, can be easily removed in acidic media. In $Si(Alk)_3$ groups, the three alkyl groups can be the same or different from each other, in particular they can be three methyl or ethyl groups or a t-butyl group and two methyl groups (i.e. a t-butyldimethylsilyl (i) group).

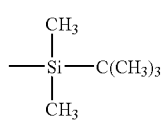

When the starting 17-oxo steroid has formula II in which R° is hydrogen or an alkali-stable protecting group, the reaction affords a 17α-(5-hydroxypentyn-1-yl)-estra-1,3,5(10)-trien-3,17β-diol of formula IV (IV)

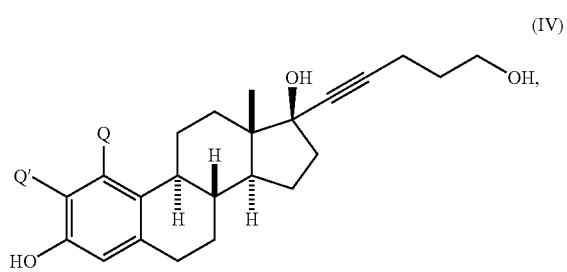

or the corresponding $\Delta^6$, $\Delta^8$, $\Delta^{9(11)}$ or $\Delta^{6,8}$ derivatives, which are both intermediates for the preparation of their 3- and 17β-esters, in particular their 5'-esters, and of interesting active principles with cicatrising action and poor or undetectable systemic activity.

When the starting 17-oxo steroid has formula I in which R° is the R'a group, the reaction affords a 17α-(5-hydroxypentyn-1-yl)-estra-1,3,5(10)-trien-3,17β-diol of formula V, (V)

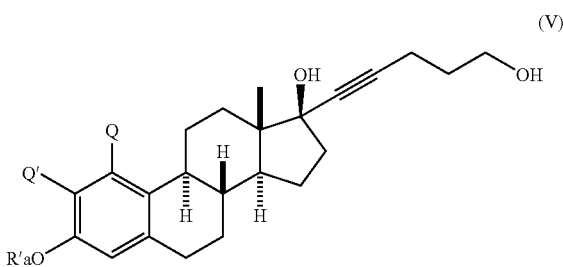

in which $R'^a$ is as defined above, or the corresponding $\Delta^6$, $\Delta^8$, $\Delta^{9(11)}$ or $\Delta^{6,8}$ derivatives, which are both intermediates for the preparation of their 17β-esters, in particular their 5'-esters, and of interesting active principles with cicatrising action and poor or undetectable systemic activity.

The resulting compounds of formula I, in which Y is ethynylene, R and R" are both hydrogen and R' is different from lower alkanoyl, can be subjected to acylation and deacylation reactions, as disclosed in U.S. Pat. No. 3,265,718, to obtain the corresponding compounds of formula I in which at least one of the R, R' and R" groups, as defined above, is an ester group.

Thus, for instance, the primary hydroxy group and the phenol group of a 17α-(5-hydroxypentyn-1-yl)-1,3,5(10)-estratrien-3,17β-diol of formula IV, or a of a $\Delta^6$, $\Delta^8$, $\Delta^{9(11)}$ or $\Delta^{6,8}$ derivative thereof, are easily and simultaneously esterified, by treatment with a lower alkanoic acid reactive derivative, such as a chloride or anhydride, optionally in the presence of a tertiary organic base such as pyridine, at room temperature or under reflux, to give the corresponding lower 3,5'-dialkanoates.

Selective esterification of the primary 5'-hydroxy group of the compound of formula IV or of a $\Delta^6$, $\Delta^8$, $\Delta^{9(11)}$ or $\Delta^{6,8}$ derivative thereof can be carried out by heating with a free acid, in particular a lower aliphatic carboxylic acid.

However, the preparation of monoesters at the primary 5'-hydroxy group is preferably carried out by reacting a compound of formula II, in which R' is a protecting group P°, with a protected alkali-metal derivative of 5-pentynol (III) with an, then treating the resulting intermediate product of formula (Ia)

(Ia)

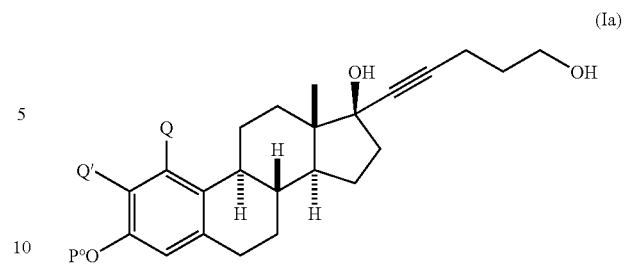

in which P°, Q and Q' are as defined above, optionally $\Delta^6$, $\Delta^8$, $\Delta^{9(11)}$ or $\Delta^{6,8}$,
with a carboxylic acid reactive derivative of formula AcOH, in which Ac is as defined above and finally removing the P° group of the resulting product of formula Ib (Ib)

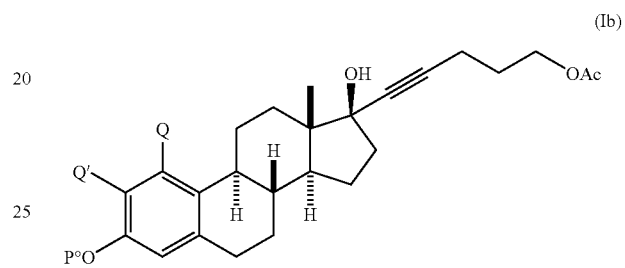

in an acidic medium, for example by treatment with p-toluenesulfonic acid, to isolate a compound of formula Ic (Ic)

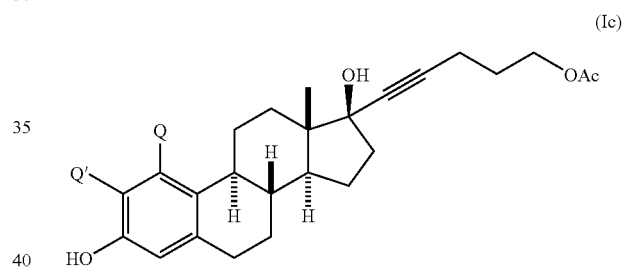

in which Q, Q' and Ac are as defined above.

In particular, the Ac group includes the lower alkanoyl groups defined above and chloroacetyl, bromoacetyl, chloropropionyl, bromopropionyl, benzoyl, 4-methoxybenzoyl, 3,4-dimethoxybenzoyl, phenylacetyl, 3-phenylpropionyl, 3-cyclopropylpropionyl, 3-cyclopentylpropionyl, 3-carboxypropionyl, 3-methoxycarbonylpropionyl, 3-ethoxycarbonyl-propionyl, cinnamoyl, nicotinoyl, isonicotinoyl groups.

The 5'-esters of formula Ic are interesting active principles with cicatrising activity and poor or undetectable estrogenic systemic side-effects.

Esterification of the tertiary hydroxy group (17β-OH) is carried out under drastic conditions, by prolonged heating of the mixture comprising compound (IV) and the R—OH acid functional derivative, followed by selective saponification of the resulting di- or triesters to give the 17-monoester only.

The compounds of formula I in which Y is ethenylene can be prepared through partial hydrogenation of the ethynylene group. Hydrogenation can be carried out in the presence of a catalyst such as palladium on charcoal or palladium hydroxide over strontium carbonate. When hydrogenation is carried out with lithium aluminium hydride, the trans derivative is obtained.

The compounds of formula I in which Y is ethylene, or a corresponding $\Delta^6$, $\Delta^8$, $\Delta^{9(11)}$ or $\Delta^{6,8}$ derivative thereof, can be prepared by reacting a compound of formula II, in which R° is different from hydrogen, or a $\Delta^6$, $\Delta^8$, $\Delta^{9(11)}$ or $\Delta^{6,8}$ derivative thereof, with 5-trimethylsilyloxy-n-pentyllithium, according to the method disclosed in U.S. Pat. No. 3,303,205 for the preparation of 17α-(3-hydroxy-n-propyl)-estradiol and 17α-(3-hydroxy-n-butyl)-estradiol. Typically, 5-trimethylsilyloxy-n-pentyl chloride is reacted with finely divided lithium in tetrahydrofuran and the mixture containing 5-trimethylsilyloxy-n-pentyllithium is added with a solution of 17-oxosteroid in a solvent conventionally used in Grignard reactions, for example tetrahydrofuran, to obtain the corresponding 17α-(5-hydroxy-n-pentyl)-estradiol derivative.

Preferred compounds according to the present invention are those of formula I'

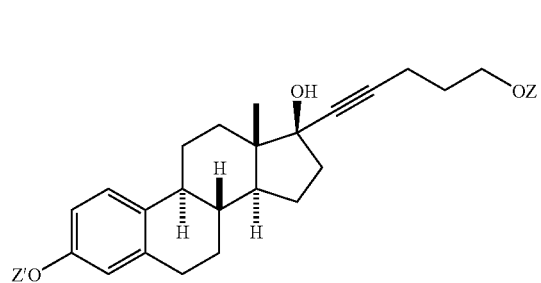

(I')

in which Z and Z' are each hydrogen or lower alkanoyl.

The compounds of formula I' in which Z' is hydrogen and Z is hydrogen or lower alkanoyl are particularly interesting.

According to a further aspect, the present invention relates to a process for the preparation of the compounds of formula I', which comprises:

(a) treating the 3-protected estrone of formula II'

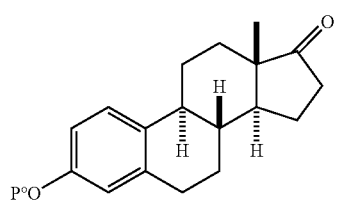

(II')

in which P° is an alkali-stable protecting group,
with a 5-pentynol derivative with an alkali metal of formula III'

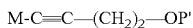

$$M\text{-}C{\equiv}C\text{-}(CH_2)_2\text{-}OP'$$ (III), in which M is an alkali metal and P' is an alkali-stable protecting group, (b) subjecting the resulting compound of formula

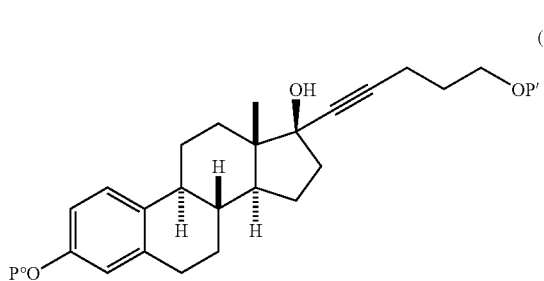

(I")

in which P° and P' are as defined above, to total or partial deprotection and recovering a compound of formula I'a, I'b or I'c (I'a)

(I'b)

(I'c)

in which P° and P' are as defined above;

(c) optionally treating the resulting compound of formula I'a, I'b or I'c with a reactive derivative of an alcanoic acid Alk-OH to obtain a compound of formula I'd, I'e or I'f (I'd)

(I'e)

-continued

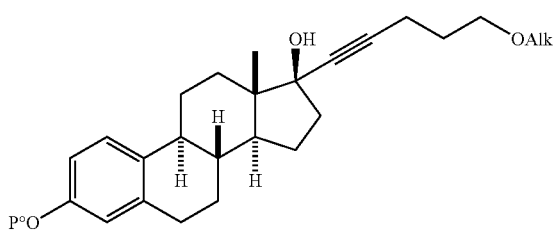

(I'f)

in which P°, P' and Alk are as defined above;

(d) optionally removing the protecting group P° or P' of the compounds of formula I'e and I'f to obtain the compound of formula I'g or I'h

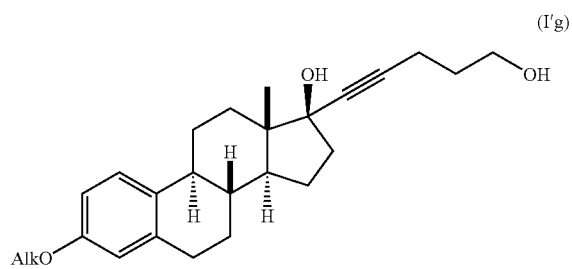

(I'g)

(I'h)

in which Alk is as defined above; and (e) optionally treating the resulting compound of formula I'g or I'h in which Alk has the meaning defined above, with a reactive derivative of an alkanoic acid Alk'-OH to obtain an asimmetric diester of formula I'i or I'j

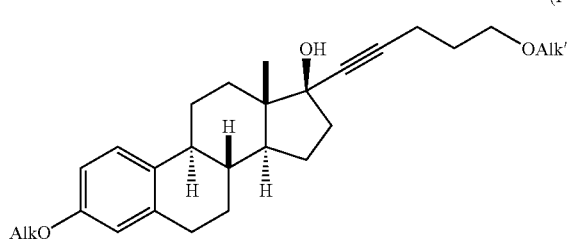

(I'i)

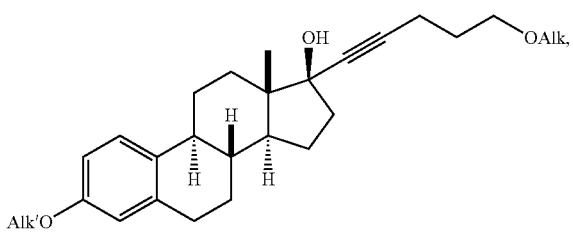

(I'j)

in which Alk and Alk' are lower alkanoyl groups different from each other.

The P° and P' protecting groups as defined above are stable in alkali and can be the same or different from each other.

Said alkali-stable protecting groups, such as 2-tetrahydropyranyl or silyl groups, in particular Si(Alk)$_3$ groups, in which Alk is lower alkyl and in which the three alkyl groups can be the same or different, in particular three methyl or ethyl groups or a t-butyl group and two methyl groups, can be easily removed with acids.

The preparation of 17-oxosteroid II' 3-tetrahydropyranyl ether (P°=2-tetrahydropyranyl) or of 5-pentynol 5-tetrahydropyranyl ether for the preparation of the alkali derivative III' (P'=2-tetrahydropyranyl) can be carried out by treating compound II or III with dihydropyran as described in J. Am. Chem. Soc. 1972, 94, 1438.

The preparation of silyl derivatives of 17-oxosteroid II (P°=trialkylsilyl) or of 5-trialchilsilyloxy-1-pentyne III"

$$HC{\equiv}C{-}(CH_2)_2{-}CH_2O{-}SiAlk_3 \qquad (III'')$$

can be carried out by treating estrone or 5-pentynol with known silylating reactives, for example trimethylsilyl chloride, triethylsilyl chloride, hexamethyldisilazane or t-butyldimethylsilyl chloride as described by T. W. Greene et al. in "Protecting groups in Organic Synthesis, 3$^{rd}$ Edition, J. Wiley & Sons, 1999", pages 113-148. The removal of said silylating groups is also disclosed therein.

In step (a) of the process of the present invention, compound III' is generally prepared in situ. Typically, the 3-protected estrone and protected 5-pentynol are reacted in a solvent suitable for Grignard reactions, for example tetrahydrofuran, at low temperature, for example from -70 to -80° C., in the presence of butyllithium dissolved in a hydrocarbon solvent, such as hexane or cyclohexane.

Compounds of formula II' and III' in which P° and P' are the same will be used for the preparation of a compound of formula I' in which Z and Z' are both hydrogen, whereas compounds of formula II' and III' in which protecting groups P° and P' are different and removable in different conditions will be used for the preparation of a compound of formula I' in which one of Z and Z' is hydrogen which is substituted, for example esterified, and the other one is a protecting group that is subsequently removed.

When protecting groups P° and P' are different, P° is preferably 2-tetrahydro pyranyl, which is easily removable with p-toluenesulfonic acid, and P' is preferably t-butyldimethylsilyl (TBDMS), which can be selectively removed in the presence of a tetrahydropyranyl group, by treatment with tetrabutylammonium fluoride according to the method described in J. Am. Chem. Soc. 1972, 94, 6190.

For the preparation the most interesting compounds of formula I', in which Z' is hydrogen and Z is hydrogen or lower alkanoyl, in the starting compound II' PI is tetrahydropyranyl and P' is TBDMS.

At the end of step (a) a compound of formula I'' is obtained.

In step (b), the compound of formula I'' is subjected to total or partial deprotection.

In the case of partial deprotection, it is necessary to use a compound of formula I'' in which substituents P° and P' are alkali-stable protecting groups, different from each other and selectively removable.

Preferably, the substituent to be removed first is the TBDMS group and the other one is the 2-tetrahydropyranyl group.

In particular, a compound of formula I'' in which P° is tetrahydropyranyl and P' is TBDMS is reacted with tetrabutylammonium fluoride. Typically, a tetrahydrofuran solution of said compound is cold-treated with a tetrabutylammonium fluoride solution and left at 20-30° C. for about two hours, until disappearance of the starting product. After deprotection a compound of formula I'a is obtained.

When a compound of formula I″ in which P° is TBDMS and P′ is tetrahydro pyranyl, said compound is reacted with tetrabutylammonium fluoride as illustrated above. After deprotection a compound of formula I′b is obtained.

In the case of total deprotection, a compound of formula II″ can be used in which substituents P° and P′ are identical alkali-stable protecting groups, for example a tetrahydropyranyl group or a —Si(Alk)$_3$ radical. When total deprotection is complete, the compound of formula I′c is obtained, which is a final product of formula I′ wherein Z and Z′ are both hydrogen, but is also a useful intermediate for the preparation of symmetrical 3,5′-diesters.

In step (c), the product of step (b) is treated with a reactive derivative of the acid Ac—OH. "Reactive derivative" means an active derivative of acid Ac—OH, which can be either commercially available, such as acetic, propionic, butyric or valeric anhydride, or an active derivative that can be prepared separately, such as an acyl chloride or an active ester, or in situ by activation with suitable reactives such as mercapto benzothiazole, dicyclohexylcarbodiimide, hydroxybenzotriazole or benzotriazole-1-yloxy-tris(dimethylamino)phosphonium hexafluorophosphate (BOP).

The reaction is carried out according to conventional esterification methods. Typically, compound I′a, I′b, or I′c is treated with an Alk-OR-Alk anhydride in the presence of a tertiary base, such as pyridine at a temperature from 20 to 40° C.

At the end of esterification of compound I′c the symmetric 3,5′-diester of formula I′d is obtained and recovered, since it is a final product of formula I′ in which Z and Z′ are identical lower alkanoyl groups.

Compounds I′b and I′a afford, respectively, 5′-protected-3-monoesters of formula I′a and 3-protected-5′-monoesters of formula I′f, which are subjected to step (d).

In step (d), the protecting groups of 3-protected 5′-monoesters and 5′-protected-3-monoesters are removed as illustrated above and the compounds of formula I′g and I′h are thus recovered. Compounds I′g and I′h are final products of formula I′. In particular, compound I′g is a product of formula I′ in which Z is lower alkanoyl and Z′ is hydrogen, and compound I′h is a product of formula I′ in which Z is hydrogen and Z′ is lower alkanoyl, but both are useful intermediates for the preparation of asymmetric 3,5′-diesters when subjected to step (e).

In step (e), the compounds of formula I′g and I′h are treated with a reactive derivative of an alcanoic acid Alk′-OH different from the acid Alk-OH used in step (c). When the esterification is complete, asymmetric esters of formula I′i and I′j are obtained, which are final products of formula I′ in which Z and Z′ are different lower alkanoyl groups.

The activity of two compounds of the invention, 17α-(5-acetoxy)pent-1-inyl-1,3,5(10)-estratriene-3,17β-diol and 17α-(5-propanoyl-oxy)pent-1-inyl-1,3,5(10)-estratriene-3,17β-diol, was determined in a cell culture and in a transgenic animal model using female adult ERE-luc mice which were ovariectomised or sham-operated three weeks before the experiment. This model allows the anti-inflammatory activity, effect on the estrogen receptor and wound-healing activity to be evaluated.

In the experiments in cell cultures, the two compounds tested proved to be estrogen receptor agonists.

In the animal model, 2 animals per experimental group were used in the first study. The two compounds studied behaved as estrogen receptor activators, and demonstrated anti-inflammatory and wound-healing activity. In a second study, 17α-(5-acetoxy)pent-1-inyl-1,3,5(10)-estratriene-3,17β-diol was chosen for a more detailed evaluation using 5 animals per experimental group. The results of this second study demonstrated that 17α-(5-acetoxy)pent-1-inyl-1,3,5(10)-estratriene-3,17β-diol is a compound with estrogenic activity active in the wound-healing process, said activity being qualitatively different from that of estradiol, although the efficacy of the wound-healing effect is statistically similar to that of the natural hormone.

The studies were conducted on the following experimental groups:
  non-ovariectomised, untreated animals (second study only);
  non-ovariectomised animals treated with the test compound (100 μL of a 100 nM/saline solution by the intradermal route in loco—second study only);
  ovariectomised control animals (subcutaneous pellet without estrogens and intradermal injection of saline);
  ovariectomised animals treated with estradiol (50 μg/kg by subcutaneous implanted pellet 24 hours before surgery);
  ovariectomised animals treated with the test compound (100 μL of a 100 nM/saline solution by the intradermal route in loco).

Each of the two test compounds was dissolved immediately before use in 99% ethanol, and a 10 mM mother solution was prepared. The successive dilutions were performed in saline solution (0.9% NaCl in bidistilled water).

1 cm long incisions were made in the anaesthetised animals to evaluate the anti-inflammatory activity of the test compounds. Said incisions were not stitched, in order to analyse the inflammatory state and wound-healing 3 days after surgery. The cells labelled with the specified antibodies were counted with the "imaging plus" program in the wound and the portion of dermis surrounding it. The macrophages were labelled with Mac3. The neutrophils were labelled with antiLy6g. In the first study, the two test compounds presented an activity quantitatively similar to that of estradiol.

The activity on the estrogen receptor was evaluated by photometric analysis with CCD chamber after 0, 24, 48 and 72 hours. The animals were then killed, and the tissue surrounding the wound was removed. In the cutaneous wound, the activity of the two test compounds was indistinguishable from that of subcutaneous estradiol, thus confirming the agonistic activity on estrogen receptors found in the cultured cells. The test conducted with a CCD camera also showed that under these experimental conditions, 17α-(5-acetoxy)pent-1-inyl-1,3,5(10)-estratriene-3,17β-diol does not have a detectable estrogenic effect in areas other than the area of administration (in particular, it does not present uterotrophic activity), whereas a slight systemic activity is performed by 17α-(5-propanoyloxy)pent-1-inyl-1,3,5(10)-estratriene-3,17β-diol.

Histological sections were prepared from the tissue surrounding the wound to evaluate the wound-healing activity. For the histological preparation, the tissue was fixed in 10% formalin (in buffer solution) and embedded in paraffin wax. The sections were stained with haematoxylin-eosin to evaluate the state of inflammation and wound-healing. The sections were also used to quantify the state of infiltration of the macrophages 4 days after the wound, using anti-Mac2 antibodies, and for further staining designed to detect the state of wound-healing and characterise the cells present in the wound area. The two compounds according to the invention proved to posses wound-healing activity similar to that of estradiol.

In the second study, which evaluated the expression of various inflammation markers (MIF, CD74, TGF-β and IL-6), it was observed that 17α-(5-acetoxy)pent-1-inyl-1,3,5(10)-estratriene-3,17β-diol has an effect profile qualitatively different from that of estradiol. The natural hormone proved to limit the expression of all the inflammation proteins studied, whereas the compound according to the invention significantly inhibited the expression of MIF, CD74 and TGF-β, but not IL-6.

The qualitative difference between estradiol and the compound according to the invention was confirmed by the comparative evaluation of the two compounds on the expression of α and β estrogen receptors (ERα and ERβ) illustrated by AM Brzozowski et al. in "Molecular basis of agonism and antagonism in the estrogen receptor" Nature 1997, 389, 753-758 (Brzozowski 1997).

17β-estradiol and 17α-(5-acetoxy)pent-1-inyl-1,3,5(10)-estratriene-3,17β-diol according to the invention have significantly different effects on the expression of estrogen receptors. Against a significant reduction in the number of α receptors, and a visible (though not significant) reduction in β receptors caused by the ovariectomy, estradiol treatment increases the number of cells that test positive for both receptors, while the 17α-(5-acetoxy)pent-1-inyl-1,3,5(10)-estratriene-3,17β-diol according to the invention does not act on the number of cells that test positive for the α receptor, and does not significantly reduce the number of cells that express the β receptor.

On the basis of said experimental findings, the compounds according to the invention are potential new-generation wound-healing agents with marked anti-inflammatory activity and low systemic estrogenic activity, or at any event below the detection limits, and are useful for local wound treatment in particular.

Thus, according to another aspect thereof, this invention provides pharmaceutical compositions which include as one of their active principles a pharmacologically effective amount of a 17α-(5-hydroxy-$C_5$-hydrocarbyl)-1,3,5(10)-estratriene-3,17β-diol derivative of formula I above, wherein Q, Q', R, R' and Y are as defined above and wherein double bonds may also be present at the 6-position, 8-position, 9(11)-position or 6- and 8-steroid positions, mixed with a pharmaceutical excipient. Active principles which are particularly useful for the compositions according to the invention are compounds of formula I' above, wherein Z and Z' are hydrogen or a lower alkanoyl. The preferred active constituents are compounds of formula I' wherein Z' is hydrogen and Z is a lower alkanoyl, in particular acetyl.

In the pharmaceutical compositions according to the invention designed for oral, subcutaneous, transdermal or topical administration, the active principles, which are 17α-(5-hydroxy-$C_5$-hydrocarbyl)-1,3,5(10)-estratriene-3,17β-diol derivatives, are preferably administered mixed with conventional pharmaceutical vehicles or excipients. The dose can vary widely, according to the size and severity of the patient's wound. This dosage comprises the administration of a dose of a 17α-(5-hydroxy-$C_5$-hydrocarbyl)-1,3,5(10)-estratriene-3,17β-diol derivative between 0.1 and 50 mg, advantageously between 1 and 25 mg, and preferably between 2.50 and 15 mg, one to three times a day, by the subcutaneous, oral, transdermal or topical route.

Pharmaceutical compositions including a 17α-(5-hydroxy-$C_5$-hydrocarbyl)-1,3,5(10)-estratriene-3,17β-diol derivative like those illustrated above are formulated with the conventional excipients suitable for the various administration routes. Formulations in the form of creams, ointments, fatty ointments, gels, foams, balsams, solutions or suspensions suitable for local administration are particularly advantageous. The compositions for local administration, such as skin solutions or suspensions, creams, ointments or fatty ointments, contain the active constituent in the percentage of 0.001 to 10%, formulated in a mixture with the conventional excipients. The excipients for creams, ointments and fatty ointments may be water, higher alkyl alcohols such as stearyl alcohol; their esters; wool alcohol; alkylene glycols such as ethylene, propylene or hexylene glycol; their mono- or diesters, such as a palmitate or stearate thereof; glycerin; its mono or diesters, such as its mono- or distearate; polyoxyalkylenes and their esters or ethers; waxes, such as white wax; paraffin wax, liquid paraffin or soft paraffin; isoparaffin or its derivatives; lanolin, lanolin alcohols and their esters, cinnamic acid esters; sorbitan tripalmitate or trioleate; polyoxyethylene sorbitan monostearate; polysorbates; dimethylsiloxane polymers. Skin lotions or solutions consist of aqueous suspensions or solutions containing alcohols such as ethanol, isopropanol or benzyl alcohol; glycols, such as propylene glycol, or their ethers or esters; cellulose derivatives, such as hydroxypropylcellulose; and buffers, such as phosphate buffer. The constituents may include preservatives such as alkyl p-hydroxybenzoates, or phenols such as butylhydroxyanisol.

The compositions according to the invention may also contain at least one other active constituent selected from antibiotics, such as neomycin, neomycin sulphate, bacitracin, and bacitracin zinc; antifungals such as miconazole and econazole; antibacterials such as chlorhexidine and its salts, in particular the gluconate, or antiseptics such as quaternary ammonium salts. In particular the compositions according to the invention can advantageously include at least one other active constituent selected from among neomycin sulphate, bacitracin zinc and chlorhexidine gluconate.

Finally, according to a further aspect, this invention provides a wound-healing method in mammals which comprises the administration to said mammal requiring wound-healing of an effective amount of a 17α-(5-hydroxy-$C_5$-hydrocarbyl)-1,3,5(10)-estratriene-3,17β-diol derivative of formula I shown above, wherein Q, Q', R, R' and Y are as defined above and wherein double bonds may also be present at the 6-position, 8-position, 9(11)-position or 6- and 8-steroid positions, in particular a compound of formula I' above, wherein Z and Z' are hydrogen or a lower alkanoyl, preferably a compound of formula I' wherein Z' is hydrogen and Z is a lower alkanoyl, preferably acetyl. The 17α-(5-hydroxy-$C_5$-hydrocarbyl)-1,3,5(10)-estratriene-3,17β-diol derivative will preferably be administered locally by applying a pharmaceutical composition as described above to the wound.

According to the present invention, the administration of the 17α-(5-hydroxy-$C_5$-hydrocarbyl)-1,3,5(10)-estratriene-3,17β-diol derivative can take place simultaneously or sequentially with that of at least one other active constituent selected from those described above.

The following examples illustrate the invention.

PREPARATION I 5-(t-Butyldimethylsilyloxy)pent-1-yne

A solution of 2.2 ml (0.024 moles) of commercial 5-hydroxy-1-pentyne and 4.0 g (0.059 moles) of imidazole and 4.01 g (0.026 moles) of t-butyldimethylsilyl chloride in 4 ml of dimethylformamide is left under stirring at room temperature (20-30° C.) until TLC (3/7 diethyl ether/petroleum ether) reveals disappearance of starting 5-hydroxy-1-pentyne and appearance of a spot with higher Rf. Usually, the disappearance of the starting product is observed after about 4 hours. The reaction mixture is diluted with water, the aqueous phase is extracted with ethyl ether and the combined organic phases are washed with a saturated sodium chloride solution and dried over anhydrous sodium sulfate. After solvent evaporation and distillation of the crude product under reduced pressure, 2.791 g (0.014 moles) of 5-(t-butyldimethylsilyloxy) pent-1-yne which distils at 67° C. at 23 mbars is obtained. Yield: 58%.

$^1$H-NMR (CDCl$_3$): δ 3.71 (t, 2H), 2.29 (td, 2H), 1.93 (t, 1H), 1.74 (q, 2H), 0.90 (s, 9H), 0.05 (s, 6H).

PREPARATION II

5-(t-Butyldimethylsilyloxy)pent-1-yne

A mixture of 186 ml of dimethylformamide, 93.5 g of 5-hydroxy-1-pentyne and 185.5 g of imidazole at room temperature (20-30° C.) is added with 185.5 g of t-butyldimethylsilyl chloride, in portions and under stirring, keeping this temperature with cooling bath. The resulting pale-yellow, dense suspension is cooled to 2° C., kept under stirring and monitored by TLC (eluent 7/3 diethyl ether/petroleum ether, developer: hot perchloric acid; Rf of the starting product=0.33, Rf of the final product=0.95); the reaction is complete after two hours. The reaction mixture is slowly added with 375 ml of water and 150 ml of toluene, and stirring is continued for 10 minutes, controlling the temperature with cooling bath. The organic phase is separated, the aqueous one is extracted with 100 ml of toluene, then combined organic phases are filtered under reduced pressure through Celite, washing the cake with 50 ml of toluene. The solution is concentrated under reduced pressure to obtain a pale-yellow oily residue which is distilled at a temperature-ranging from 23 to 34° C. at about 13 mbars and subsequently at 7.5 mbars at a temperature ranging from 35 to 60° C. The two resulting fractions are discarded. Continuing the distillation at 7.5 mbars, the fractions which distil above 60° C. are collected. The first fraction, which distils between 60 and 75° C. (89 g) is in turn discarded whereas the second one, which distils at 75° C., consists of 101 g of 5-(t-butyldimethylsilyloxy)pent-1-yne identical to the product of preparation I.

PREPARATION III

Estrone 3-tetrahydropyranyl ether

A solution of 2.00 g (7.4 mmoles) of estrone in 35 ml of dry dichloromethane, cooled to 0° C. under argon atmosphere and magnetic stirring, is added with 2.7 ml (0.03 moles) of dihydropyran (3,4-dihydro-2H-pyran) and 0.014 g (0.075 mmoles) of p-toluenesulfonic acid. After 10 minutes under the same conditions, the mixture is brought to room temperature (20-30° C.) and stirring is continued until TLC (1/1 ethyl ether/hexane) reveals disappearance of the starting product and a spot with higher Rf. Usually, the reaction is complete after about 1 hour. The reaction mixture is then diluted with dichloromethane and washed with a saturated NaHCO$_3$ solution. The aqueous phase is extracted with dichloromethane and the combined organic phases are washed with a saturated sodium chloride solution and dried over anhydrous sodium sulfate. After complete evaporation of the solvent under reduced pressure, the residue is crystallized from methanol to obtain 2.5 g. (0.007 moles) of estrone tetrahydropyranyl ether. Yield: 95%.

$^1$H-NMR (CDCl$_3$): δ 7.19 (d, 1H), 6.78-6.90 (m, 2H), 5.40 (t, 1H), 3.85-4.00 (m, 1H), 3.55-3.66 (m, 1H), 2.90 (t, 2H).

PREPARATION IV

Estrone 3-tetrahydropyranyl ether 48.2 ml of dihydropyran are added drop by drop to a mixture of 36.23 g of estrone and 580 ml of dichloromethane cooled to 2° C., under nitrogen atmosphere and with stirring. The mixture is stirred at this temperature for 10 minutes, then brought to room temperature (20-30° C.) and stirred again, monitoring by TLC (eluent: 1/1 diethyl ether/petroleum ether, developer: hot perchloric acid; Rf of the starting product=0.29, Rf of the resulting estrone tetrahydropyranyl ether=0.50). After about 90 minutes the reaction is complete and the mixture is added under stirring with 275 ml of dichloromethane and 300 ml of a saturated NaHCO$_3$ solution (pH=7.9). The mixture is left under stirring for 10 minutes, then the organic phase is separated and the aqueous one is extracted with dichloromethane. The combined organic phases are washed with 150 ml of a saturated NaCl solution and concentrated to dryness under reduced pressure. The crude product (60.5 g) is suspended in 120 ml of methanol and 70 ml of this mixture are distilled off under reduced pressure. The remaining mixture is treated with 60 ml of methanol and kept under stirring at 40° C. for 10 minutes, then cooled to 0° C. and left under stirring for 1 hour. After filtration under reduced pressure, the solid is washed with 40 ml of methanol cooled to −10° C. and dried under reduced pressure to 35° C. 45.5 g of estrone 3-tetrahydropyranyl ether as white crystalline solid identical to the product of PREPARATION III is obtained.

EXAMPLE 1

3-Tetrahydropyranyloxy-17α-(5-t-butyldimethylsilyloxy)pent-1-ynyl-1,3,5(10)-estratrien-17β-ol (Formula I', Z'=THP, Z=—SiMe$_2$tBu)

A solution of 1.8 g (9.1 mmoles) of 5-(t-butyldimethylsilyloxy)pent-1-yne, prepared as described in PREPARATION I, in 16 ml of dry tetrahydrofuran, under argon atmosphere and magnetic stirring, at −78° C., is added with 2.7 ml of a 2.0 M solution of n-butyllithium (5.4 mmoles) in cyclohexane. After 3 hours the mixture is added with a solution of 0.50 g (1.4 mmoles) of estrone tetrahydropyranyl ether in 5 ml of dry tetrahydrofuran. After 1 hour the mixture is brought to room temperature (20-30° C.) and left under stirring until TLC (1/1 diethyl ether/petroleum ether) reveals disappearance of estrone tetrahydropyranyl ether and appearance of a new spot with higher Rf. The reaction is usually complete after about 3 hours. The reaction mixture is neutralized with 0.5 M hydrochloric acid, the aqueous phase is extracted with ethyl ether, the organic phase is washed with a saturated sodium chloride solution and dried over anhydrous sodium sulfate. After evaporation of the solvent under reduced pressure 1.7 g of crude product is obtained and purified by silica gel chromatography (product/silica ratio of 1/100) with 40/60 ethyl ether/hexane as eluent, to afford 0.60 g (1.1 mmoles) of 3-tetrahydropyranyloxy-17α-(5-t-butyldimethylsilyloxy) pent-1-ynyl-1,3,5(10)-estratrien-17β-ol. Yield: 79%.

$^1$H-NMR (CDCl$_3$): δ 7.21 (d, 1H), 6.77-6.90 (m, 2H), 5.40 (t, 1H), 3.85-4.00 (m, 1H), 3.71 (t, 2H) 3.55-3.66 (m, 1H), 2.84 (m, 2H), 0.89 (s, 9H) 0.86 (s, 3H), 0.05 (s, 6H).

EXAMPLE 2

3-Tetrahydropyranyloxy-17α-(5-hydroxy)pent-1-ynyl-1,3,5(10)-estratrien-17β-ol (Formula I', Z'=THP, Z=H)

A solution of 0.30 g (0.543 mmoles) of 3-tetrahydropyranyloxy-17α-(5-t-butyldimethylsilyloxy)pent-1-ynyl-1,3,5 (10)-estratrien-17β-ol (prepared as described in example 1) in 5 ml of tetrahydrofuran is cooled to 0° C. and added under stirring with 11.1 ml of a 1.0 M solution of tetrabutylammonium fluoride (1.1 mmoles) in tetrahydrofuran. After stirring for 10 minutes the mixture is brought to room temperature (20-30° C.) and left under stirring until TLC (70/30 diethyl ether/petroleum ether) reveals disappearance of the starting product and appearance of a spot with lower Rf. The reaction is generally complete after about 2 hours. The mixture is diluted with 30 ml of ethyl acetate, the resulting organic phase is washed with water, the aqueous phase is extracted with ethyl acetate and the combined organic phases are washed with a saturated sodium chloride solution and dried over anhydrous sodium sulfate. After evaporation of the solvent under reduced pressure, the residue (0.41 g of crude product) is purified by silica gel chromatography (product/silica ratio of 1/100) with 40/60 diethyl ether/hexane as eluent, to obtain 0.184 g (0.42 mmoles) of 3-tetrahydropyranyloxy-17α-(5-hydroxy)pent-1-ynyl-1,3,5(10)-estratrien-17β-ol. Yield: 80%.

$^1$H-NMR (CDCl$_3$): δ 7.20 (s, 1H), 6.76-6.88 (m, 2H), 5.39 (t, 1H), 3.82-4.00 (m, 1H), 3.76 (t, 2H), 3.54-3.66 (m, 1H), 2.80-2.90 (m, 2H), 0.85 (s, 3H).

EXAMPLE 3

3-Tetrahydropyranyloxy-17α-(5-acetoxy)pent-1-ynyl-1,3,5(10)-estratrien-17β-ol (Formula I, Z'=THP, Z=CH$_3$CO—)

A solution of 0.05 g (0.114 mmoles) of 3-tetrahydropyranyloxy-17β-(5-hydroxy)pent-1-ynyl-1,3,5(10)-estratrien-17β-ol prepared as described in example 2, in 1 ml of pyridine is cooled to 0° C. and added with 0.09 ml (0.95 mmoles) of acetic anhydride. The mixture is left under stirring until TLC (70/30 ethyl ether/petroleum ether) reveals disappearance of the starting product and appearance of a spot with higher Rf. The reaction mixture is diluted with ethyl ether and washed with 0.5 M hydrochloric acid. The aqueous phase is extracted with ethyl ether; the combined organic phases are washed with a saturated sodium chloride solution and dried over anhydrous sodium sulfate. After evaporation of the solvent under reduced pressure, 0.16 g of crude is obtained which is purified by silica gel chromatography (product/silica ratio of 1/100) with 30/70 ethyl ether/hexane as eluent. 0.048 g (0.10 mmoles) of 3-tetrahydropyranyloxy-17α-(5-acetoxy)pent-1-ynyl-1,3,5(10)-estratrien-17β-ol is obtained. Yield: 91%.

$^1$H-NMR (CDCl$_3$): δ 7.20 (s, 1H), 6.76-6.88 (m, 2H), 5.39 (t, 1H), 4.15 (t, 2H), 3.82-4.00 (m, 1H), 3.50-3.62 (m, 1H), 2.80-2.90 (m, 2H), 0.85 (s, 3H).

EXAMPLE 4

3-Tetrahydropyranyloxy-17α-(5-propanoyloxy)pent-1-ynyl-1,3,5(10)-estratrien-17β-ol (Formula I', Z'=THP, Z=CH$_3$CH$_2$CO—)

Following the procedure of example 3, starting from 0.080 g (0.18 mmoles) of 3-tetrahydropyranyloxy-17α-(5-hydroxy)pent-1-ynyl-1,3,5(10)-estratrien-17β-ol (prepared as described in example 2) in 2 ml of pyridine and 0.15 ml (1.2 mmoles) of propionic anhydride, 0.092 g of crude is obtained which affords 0.082 g (0.17 mmoles) of 3-tetrahydropyranyloxy-17α-(5-propanoyloxy)pent-1-ynyl-1,3,5(10)-estratrien-17β-ol. Yield: 94%.

$^1$H-NMR (CDCl$_3$): δ 7.20 (s, 1H), 6.76-6.88 (m, 2H), 5.39 (t, 1H), 4.15 (t, 2H), 3.82-4.00 (m, 1H), 3.50-3.62 (m, 1H), 2.80-2.90 (m, 2H), 1.12 (t, 3H), 0.85 (s, 3H).

EXAMPLE 5

3-Tetrahydropyranyloxy-17α-(5-butanoyloxy)pent-1-ynyl-1,3,5(10)-estratrien-17β-ol (Formula I, Z'=THP, Z=CH$_3$(CH$_2$)$_2$ CO—)

A solution of 0.075 g (0.17 mmoles) of 3-tetrahydropyranyloxy-17α-(5-hydroxy)pent-1-ynyl-1,3,5(10)-estratrien-17β-ol (prepared as described in example 2) in 2 ml of pyridine is cooled to 0° C. and added with 0.28 ml (0.17 mmoles) of butyric anhydride. The mixture is left under stirring until TLC (70/30 ethyl ether/petroleum ether) reveals disappearance of the starting product and appearance of a spot with higher Rf (about 24 hours). The reaction mixture is diluted with ethyl ether and washed with 0.5 M hydrochloric acid. The aqueous phase is extracted with ethyl ether and the combined organic phases are washed with a saturated sodium chloride solution and dried over anhydrous sodium sulfate. After evaporation of the solvent under reduced pressure 0.226 g of crude product is obtained which, after silica gel chromatography (product/silica ratio of 1/100) with 30/70 ethyl ether/hexane as eluent, yields 0.083 g (0.163 mmoles) of 3-tetrahydropyranyloxy-17α-(5-butanoyloxy)pent-1-ynyl-1,3,5(10)-estratrien-17β-ol. Yield 94%.

$^1$H-NMR (CDCl$_3$): δ 7.21 (d, 1H), 6.76-6.88 (m, 2H), 5.36-5.42 (m, 1H), 4.18 (t, 2H) 3.85-4.00 (m, 1H), 3.52-3.66 (m, 1H), 2.78-2.90 (m, 2H), 0.94 (t, 3H) 0.85 (s, 3H).

EXAMPLE 6

3-Tetrahydropyranyloxy-17α-(5-pentanoyloxy)pent-1-ynyl-1,3,5(10)-estratrien-17β-Sol (Formula I', Z'=THP, Z=CH$_3$(CH$_2$)$_3$ CO—)

A solution of 0.061 g (0.14 mmoles) of 3-tetrahydro pyranyloxy-17α-(5-hydroxy)pent-1-ynyl-1,3,5(10)-estratrien-17β-ol (prepared as described in example 2 in 2 ml of pyridine) is cooled to 0° C. and added with 0.27 ml (1.3 mmoles) of valeric anhydride. The mixture is left under stirring until TLC (70/30 ethyl ether/petroleum ether) reveals disappearance of the starting product and appearance of a spot with higher R$_f$ (about 24 hours). The reaction mixture is diluted with ethyl ether and washed with 0.5 M hydrochloric acid. The aqueous phase is extracted with ethyl ether; the combined organic phases are washed with a saturated sodium chloride solution and dried over anhydrous sodium sulfate. After evaporation of the solvent under reduced pressure, 0.26 g of crude is obtained and purified by silica gel chromatography (product/silica ratio of 1/100) with 30/70 ethyl ether/hexane as eluent, to obtain 0.069 g (0.13 mmoles) of 3-tetrahydropyranyloxy-17α-(5-pentanoyloxy)pent-1-ynyl-1,3,5(10)-estratrien-17β-ol. Yield: 93%.

$^1$H-NMR (CDCl$_3$): δ 7.21 (d, 1H), 6.76-6.88 (m, 2H), 5.36-5.42 (m, 1H), 4.18 (t, 2H), 3.85-4.00 (m, 1H), 3.52-3.66 (m, 1H), 2.78-2.90 (m, 2H), 0.86 (s, 3H).

EXAMPLE 7

17α-(5-acetoxy)pent-1-ynyl-1,3,5(10)-estratrien-3, 17α-diol (Formula I', Z'=H, Z=CH$_3$CO—)

A mixture of 0.0326 g (0.069 mmoles) of 3-tetrahydropyranyloxy-17α-(5-acetoxy)pent-1-ynyl-1,3,5(10)-estratrien-17β-ol prepared as described in example 3, and of a 1.3 mM solution of p-toluenesulfonic acid in methanol is left under stirring until TLC (70/30 ethyl ether/petroleum ether) reveals disappearance of the starting product and appearance of a spot with lower Rf (about 2 hours). The reaction mixture is neutralized with a cold saturated NaHCO$_3$ solution. The aqueous phase is extracted with ethyl ether, the organic phase is washed with a saturated sodium chloride solution and dried over anhydrous sodium sulfate. After evaporation of the solvent under reduced pressure, 0.043 g of crude product is obtained and purified by silica gel chromatography (product/silica ratio of 11100) with 35/65 ethyl ether/hexane as eluent, to obtain 0.02 g (0.05 mmoles) of 17α-(5-acetoxy)pent-1-ynyl-1,3,5(10)-estratrien-3,17β-diol. Yield: 73%.

$^1$H-NMR (CDCl$_3$): δ 7.14 (d, 1H), 6.55-6.74 (m, 2H), 4.19 (t, 2H), 2.70-2.88 (m, 2H), 0.87 (s, 3H).

EXAMPLE 8

17α-(5-Propanoyloxy)pent-1-ynyl-1,3,5(10)-estratrien-3,17β-diol (Formula I', Z'=H, Z=CH$_3$CH$_2$CO—)

Following the procedure of example 7, starting from 0.080 g (0.16 mmoles) of 3-tetrahydropyranyloxy-17α-(5-propanoyloxy)pent-1-ynyl-1,3,5(10)-estratrien-17β-ol prepared as described in example 4 and from a 3.2 mM solution of p-toluenesulfonic acid in methanol, 0.075 g is obtained and purified by silica gel chromatography (product/silica ratio of 1/100) with 30/70 ethyl ether/hexane as eluent, to give 0.064 g (0.156 mmoles) of 17α-(5-propanoyloxy)pent-1-ynyl-1,3,5(10)-estratrien-3,17β-diol. Yield: ~100%.

$^1$H-NMR (CDCl$_3$): δ 7.14 (d, 1H), 6.55-6.74 (m, 2H), 4.17 (t, 2H), 2.70-2.91 (m, 2H), 1.12 (t, 3H), 0.85 (s, 3H).

EXAMPLE 9

17α-(5-Butanoyloxy)pent-1-ynyl-1,3,5(10)-estratrien-3,17β-ol (Formula I', Z'=H, Z=CH$_3$(CH$_2$)$_2$CO—)

Following the procedure of example 7, starting from 0.07 g (0.14 mmoles) of 3-tetrahydropyranyloxy-17α-(5-butanoyloxy)pent-1-ynyl-1,3,5(10)-estratrien-17β-ol prepared as described in example 5 and from a 1.95 mM solution of p-toluenesulfonic acid in methanol, 0.06 g of crude product is obtained and purified by silica gel chromatography (product/silica ratio of 1/100) with 30/70 ethyl ether/hexane as eluent, to give 0.050 g (0.118 mmoles) of 17α-(5-butanoyloxy)pent-1-ynyl-1,3,5(10)-estratrien-3,17β-diol. Yield: 86%.

$^1$H-NMR (CDCl$_3$): δ 7.16 (d, 1H), 6.55-6.66 (m, 2H), 5.14 (s, 1H), 4.19 (t, 2H) 2.75-2.88 (m, 2H), 0.94 (t, 3H), 0.87 (s, 3H).

EXAMPLE 10

17α-(5-Pentanoyloxy)pent-1-ynyl-1,3,5(10)-estratrien-3,17β-diol (Formula I', Z'=H, Z=CH$_3$(CH$_2$)$_3$CO—)

Following the procedure of example 7, starting from 0.052 g (0.099 mmoles) of 3-tetrahydropyranyloxy-17α-(5-pentanoyloxy)pent-1-ynyl-1,3,5(10)-estratrien-17β-ol prepared as described in example 6 and from a 1.98 mM solution of p-toluenesulfonic acid in methanol, 0.045 g of crude product is obtained and purified by silica gel chromatography (product/silica ratio of 1/100) with 30/70 ethyl ether/hexane as eluent, to give 0.039 g (0.089 mmoles) of 17α-(5-pentanoyloxy)pent-1-ynyl-1,3,5(10)-estratrien-3,17β-diol. Yield: 90%.

$^1$H-NMR (CDCl$_3$): δ 7.16 (d, 1H), 6.55-6.66 (m, 2H), 5.55 (s, 1H), 4.19 (t, 2H) 2.75-2.88 (m, 2H).

EXAMPLE 11

17α-(5-hydroxy)pent-1-ynyl-1,3,5(10)-estratrien-3,17β-diol (Formula I', Z'=Z=H)

A solution of 0.16 g (0.29 mmoles) of 3-tetrahydropyranyloxy-17α-(5-t-butyldimethylsilyloxy)pent-1-ynyl-1,3,5(10)-estratrien-17β-ol prepared as described in example 1 in 8 ml of tetrahydrofuran is added under stirring with 4 ml of 0.5 M hydrochloric acid and the mixture is left under stirring at room temperature (20-30° C.) until TLC (7/3 ethyl ether/petroleum ether) reveals disappearance of the reagent and appearance of a new spot with Rf~0.2. The reaction is usually complete after about 2 hours. The mixture is neutralized with a saturated NaHCO$_3$ solution and the aqueous phase is extracted with ethyl acetate. The organic phase is washed with a sodium chloride saturated solution and dried over anhydrous sodium sulfate. After evaporation of the solvent under reduced pressure the residue (0.23 g. of crude product) is purified by silica gel chromatography (product/silica ratio of 1/100) with 40/60 ethyl acetate/hexane as eluent, to give 0.097 g (0.27 mmoles) of 17α-(5-hydroxy)pent-1-ynyl-1,3,5(10)-estratrien-3,17β-diol. Yield: 94%.

$^1$H-NMR (CD$_3$OD): δ 7.06 (d, 1H), 6.43-6.68 (m, 2H), 3.66 (t, 2H), 2.68-2.82 (m, 2H), 0.83 (s, 3H).

EXAMPLE 12

3-Acetoxy-17α-(5-acetoxy)pent-1-ynyl-1,3,5(10)-estratrien-17β-ol Formula I', Z=Z'=—COCH$_3$)

A solution of 0.030 g (0.085 mmoles) of 17α-(5-hydroxy)pent-1-ynyl-1,3,5(10)-estratrien-3,17β-diol (prepared as described) in example 11, in 1 ml of pyridine is cooled to 0° C. and added with 0.090 ml (0.95 mmoles) of acetic anhydride. The mixture is left under stirring until TLC (80/20 ethyl ether/petroleum ether) reveals disappearance of the starting product and appearance of a spot with higher Rf. The reaction mixture is diluted with ethyl ether and washed with 0.5 M hydrochloric acid. The aqueous phase is extracted with ethyl ether; the combined organic phases are washed with a saturated sodium chloride solution and dried over anhydrous sodium sulfate. 0.035 g of crude product is obtained which is purified by silica gel chromatography (product/silica ratio of 1/100) with 40/60 ethyl acetate/hexane as eluent, to obtain 0.032 g (0.073 mmoles) of 3-acetoxy-17α-(5-acetoxy)pent-1-ynyl-1,3,5(10)-estratrien-17β-ol. Yield: 86%.

$^1$H-NMR (CDCl$_3$): δ 7.32 (d, 1H), 6.76-6.93 (m, 2H), 4.20 (t, 2H), 2.80-2.95 (m, 2H), 0.87 (s, 3H).

EXAMPLE 13

17α-(5-Acetoxy)pent-1-ynyl-1,3,5(10)-estratrien-3,17βdiol (a) 3-Tetrahydropyranyloxy-17α-(5-t-butyldimethylsilyloxy)pent-1-ynyl-1,3,5(10)-estratrien-17-βol A solution of 16.8 g of S-(t-butyldimethyl silyloxy)pent-1-yne, prepared as described in PREPARATION II, in 240 ml of dry tetrahydrofuran under nitrogen atmosphere, cooled to −40° C., is added drop by drop under stirring with 26 ml of butyllithium (4.1 g). The mixture is left under stirring for 60-90 minutes, then added drop by drop with a solution of 15 g of estrone tetrahydropyranyl ether (prepared as described in PREPARATION IV) in 150 ml of dry tetrahydrofuran. The mixture is left under stirring for about 30 minutes at −40° C., then the temperature is adjusted to 30° C. and stirring is continued for 6 hours at the same temperature, thereafter heating is stopped and the mixture is kept under stirring at room temperature (20-30° C.) and monitored by TLC (1/1 ethyl ether/petroleum ether as eluent, developer: hot perchloric acid; Rf of the starting product=0.50, Rf of the final product=0.70). The reaction is usually complete after 12-16-hours. The reaction mixture is neutralized with 0.2 N hydrochloric acid to pH 7, thereafter the aqueous phase is extracted with ethyl acetate (2×75 ml) and the combined organic phases are filtered through Celite, washing the cake with ethyl acetate, then concentrated under reduced-pressure to an oily residue. 31.2 g of a yellow oil comprising 3-tetrahydro pyranyloxy-17α-(5-t-butyldimethylsilyloxy)pent-1-ynyl-1,3,5(10)-estratrien-17β-ol are thus obtained.

(b) 3-Tetrahydropyranyloxy-17α-(5-hydroxy)pent-1-ynyl-1,3,5(10)-estratrien-17β-ol A solution of 31.2 g of the oil containing 3-tetrahydropyranyloxy-17α-(5-t-butyldimethylsilyloxy)pent-1-ynyl-1,3,5(10)-estratrien-17β-ol obtained in step (a) in 150 ml of tetrahydrofuran is cooled to 0° C. and added dropwise with 103 ml of a 1M solution of tetrabutylammonium fluoride in tetrahydrofuran, over 10 minutes and under stirring. After stirring for 10 minutes at 0° C. the mixture is brought to room temperature (20-30° C.), left under stirring and monitored by TLC (eluent: 7/3 ethyl ether/petroleum ether, developer: hot perchloric acid; Rf of the starting product=0.85, Rf of the final product=0.17). The reaction is complete after about 2 hours. 300 ml of ethyl acetate and 300 ml of water are added under stirring, then the aqueous phase is separated and the organic one is washed with 250 ml of water. The combined aqueous phases are extracted with ethyl acetate (2×75 ml) and the organic phase is concentrated under-reduced pressure to obtain 31 g of yellow oil. The crude product is purified by column chromatography on silica gel eluting with the following eluent gradient: (8/2) hexane/ethyl acetate, (7/3) hexane/ethyl acetate, (6/4) hexane/ethyl acetate. The combined fractions containing the reaction product are evaporated to give 14.12 g of 3-tetrahydro pyranyloxy-17α-(5-hydroxy)pent-1-ynyl-1,3,5(10)-estratrien-17β-ol as a white solid.

(c) 3-Tetrahydropyranyloxy-17α-(5-acetoxy)pent-1-ynyl-1,3,5(10)-estratrien-17β-ol 25.4 ml (27.6 g) of acetic anhydride are added drop by drop over 10 minutes into a solution of 14.12 g of 3-tetrahydropyranyloxy-17α-(5-hydroxy)pent-1-ynyl-1,3,5(10)-estratrien-17β-ol obtained in step (b) in 282 ml of pyridine. The mixture is kept under stirring for 2 hours at 0-5° C., then the temperature is raised to 16° C. and stirring is stopped. TLC (eluent: 7/3 ethyl ether/petroleum ether, developer: hot perchloric acid; Rf of the starting product=0.17, Rf of the final product=0.60) shows that the reaction is complete after 12-16 hours. The reaction mixture is added with 300 ml of ethyl acetate under vigorous stirring, then the phases are separated, the organic one is washed with 0.5 N HCl to pH 7 and the aqueous one is extracted with ethyl acetate (2×1000 ml). The organic phases are combined, filtered through Celite and concentrated to afford 37.4 g of an oil which contains 3-tetrahydropyranyloxy-17α-(5-acetoxy)pent-1-ynyl-1,3,5(10)-estratrien-17β-ol to be used in the subsequent step.

(d) 17α-(5-acetoxy)pent-1-ynyl-1,3,5(10)-estratrien-3,17β-diol

A mixture containing 37.4 g of 3-tetrahydropyranyloxy-17β-(5-acetoxy)pent-1-ynyl-1,3,5(10)-estratrien-17β-ol obtained in step (c) and a solution of 50 g of p-toluenesulfonic acid in 831 ml of methanol is added with 831 ml of water under vigorous stirring and stirring is continued monitoring the reaction by TLC (eluent: 7/3 ethyl ether/petroleum ether, developer: hot perchloric acid; Rf of the starting product=0.60, Rf of the final product=0.34). After 5 hours the reaction is complete. The reaction solution is added dropwise with 1000 ml of ethyl acetate, the organic phase is separated and the aqueous one is extracted with ethyl acetate (2×500 ml). The combined organic fractions are filtered through Celite and concentrated under vacuum to an oil. After purification by column chromatography (column diameter: 6 cm; height: 30 cm) on 250 g of silica with 6/4 hexane/ethyl acetate as eluent, 8 g of 17α-(5-acetoxy)pent-1-ynyl-1,3,5 (10)-estratrien-3,17β-diol is obtained as a white crystalline solid identical to the product of example 7.

EXAMPLE 14

17α-(5-Propanoyloxy)pent-1-ynyl-1,3,5(10)-estratrien-3,17β-diol

3-Tetrahydropyranyloxy-17α-(5-hydroxy)pent-1-ynyl-1,3,5(10)-estratrien-17β-ol obtained from step (b) of example 13 is subjected to steps (c') and (d')

(c') 3-Tetrahydropyranyloxy-17α-(5-propanoyloxy-oxy)pent-1-ynyl-1,3,5(10)-estratrien-17β-ol 15 ml of propionic anhydride are added drop by drop to a mixture of 8.1 g of 3-tetrahydropyranyloxy-17α-(5-hydroxy)pent-1-ynyl-1,3,5(10)-estratrien-17β-ol and 200 ml of pyridine, cooled to 0-2° C. The mixture is kept under stirring for 6 hours, then stirring is stopped and the mixture cooled to −16° C. and left to stand at this temperature, monitoring by TLC (eluent 7/3 ethyl ether/petroleum ether, developer: hot perchloric acid; Rf of the starting product=0.17, Rf of the final product=0.68). In an experiment, after 14 hours a −16° C. the reaction was complete. The mixture is added with 200 ml of dichloromethane and saturated NaHCO$_3$ solution under stirring until phase separation. The organic phase is separated and the aqueous one is extracted with dichloromethane (2×100 ml). The combined organic phases are washed with 100 ml of a saturated NaCl solution, filtered through Celite and concentrated to an oil. 10.4 of an oil containing 3-tetrahydropyranyloxy-17α-(5-propanoyloxy)pent-1-ynyl-1,3,5 (10)-estratrien-17β-ol to be submitted to the subsequent step are thus obtained.

(d') 17α-(5-propanoyloxy)pent-1-ynyl-1,3,5(10)-estratrien-3,17β-diol

A mixture of 10.4 g of the oil containing 17α-(5-propanoyloxy)pent-1-ynyl-1,3,5(10)-estratrien-17β-ol from step (c') and 650 ml of 0.0175 M p-toluenesulfonic acid in methanol is kept under stirring at room temperature (20-30° C.) for 8 hours, then the temperature of the mixture is cooled to −16° C. After 12-16 hours at this temperature without stirring, the mixture is brought to room temperature (20-30° C.), treated with further 1.1 g of p-toluenesulfonic acid and kept at this temperature, monitoring by TLC (eluent 7/3 ethyl ether/petroleum ether, developer: hot perchloric acid; Rf of the starting product=0.60, Rf of the final product=0.62). After 4 hours the reaction is complete. The reaction mixture is added with 650 ml of dichloromethane and 650 ml of water, then the organic phase is separated and the aqueous one is extracted with dichloromethane (2×100 ml). The combined organic phases are decolourized with charcoal, filtered through Celite and concentrated under reduced pressure to obtain 9.5 g of an oily residue which is purified by column chromatography (column diameter: 5 cm, height 30 cm) with 200 g of silica (eluent: 6:4 hexane/ethyl acetate). 5.6 g of 17α-(5-propanoyloxy)pent-1-ynyl-1,3,5(10)-estratrien-3,17β-diol as crystalline white solid is thereby recovered.

The invention claimed is:
1. A 17α-(5-Hydroxy-C$_5$-hydrocarbyl)-1,3,5(10)-estratrien-3,17β-diol derivative of formula I

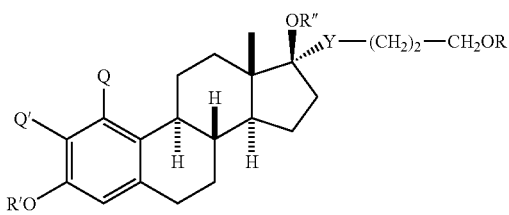

wherein Q is hydrogen or methyl, Q' is hydrogen, methyl or lower alkoxy, R is hydrogen or an acyl group selected from monocarboxylic unsaturated acyl groups containing 3 to 5 carbon atoms, saturated monocarboxylic acyl groups containing 1 to 5 carbon atoms, said acyl groups being optionally substituted with carboxy, methoxycarbonyl, ethoxycarbonyl, phenyl, tolyl, xylyl, methoxyphenyl, fluorophenyl, chlorophenyl, bromophenyl, nitrophenyl, dimethoxyphenyl, 1-naphthyl, 2-naphthyl, pyridyl, cycloalkyl from 3 to 7 carbon atoms, haloalkanoyl groups containing 2 to 5 carbon atoms, provided that the acyl group is not bromoacetyl or chloroacetyl, R' is hydrogen, lower alkanoyl, or a radical consisting of a lower alkyl or (C$_5$-C$_6$)cycloalkyl group, and R" is hydrogen or a lower alkanoyl group, Y is an ethenylene group (—CH=CH—) or an ethynylene group (—C≡C—); and wherein double bonds can also optionally be present at the 6-position, at the 8-position, at the 9(11)-position or at the 6- and 8-steroid positions.

2. The 17α-(5-Hydroxy-C$_5$-hydrocarbyl)-1,3,5(10)-estratrien-3,17β-diol derivative of claim 1, wherein Y is ethynylene.

3. The 17α-(5-Hydroxy-C$_5$-hydrocarbyl)-1,3,5(10)-estratrien-3,17β-diol derivative of claim 2, wherein R, R' and R" are hydrogen.

4. The 17α-(5-Hydroxy-C$_5$-hydrocarbyl)-1,3,5(10)-estratrien-3,17β-diol derivative of claim 2, wherein R and R" are hydrogen and R' is a lower alkyl or (C$_5$-C$_6$)cycloalkyl group.

5. The 17α-(5-Hydroxy-C$_5$-hydrocarbyl)-1,3,5(10)-estratrien -3,17β-diol derivative of claim 1, wherein the acyl group is selected from the group consisting of chloropropionyl, bromopropionyl, benzoyl, 4-methoxybenzoyl, 3,4-dimethoxybenzoyl, phenylacetyl, 3-phenylpropionyl, 3-cyclopropylpropionyl, 3-cyclopentylpropionyl, 3-carboxypropionyl, 3-methoxycarbonylpropionyl, 3-ethoxycarbonyl-propionyl, cinnamoyl, nicotinoyl, and isonicotinoyl groups.

6. The 17α-(5-Hydroxy-C$_5$-hydrocarbyl)-1,3,5(10)-estratrien-3,17β-diol derivative of claim 1, wherein Y is ethynylene, and Q, Q' and R" are hydrogen.

7. The 17α-(5-Hydroxy-C$_5$-hydrocarbyl)-1,3,5(10)-estratrien-3,17β-diol derivative of claim 6, comprising the formula I'

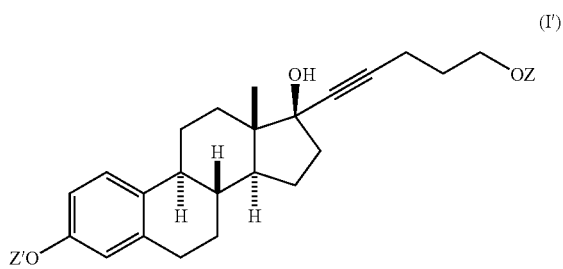

wherein Z and Z' are hydrogen or lower alkanoyl.

8. The 17α-(5-Hydroxy-C$_5$-hydrocarbyl)-1,3,5(10)-estratrien-3,17β-diol derivative of claim 1, which is 17α-(5-Hydroxypentyn-1-yl)-1,3,5(10)-estratrien-3,17β-diol.

9. The 17α-(5-Hydroxy-C$_5$-hydrocarbyl)-1,3,5(10)-estratrien-3,17β-diol derivative of claim 1, which is 17 α-(5-Acetoxypentyn-1-yl)-1,3,5(10)-estratrien-3,17 β-diol.

10. The 17α-(5-Hydroxy-C$_5$-hydrocarbyl)-1,3,5(10)-estratrien-3,17β-diol derivative of claim 1, which is 17 α-(5-Propanoyloxypent-1-yl)-1,3,5(10)-estratrien-3,17 β-diol.

11. A pharmaceutical composition containing, as active ingredient, a 17α-(5-hydroxy-C$_5$-hydrocarbyl)-1,3,5(10)-estratrien-3,17β-diol derivative of claim 1, in admixture with a pharmaceutical excipient.

12. The pharmaceutical composition of claim 11, wherein said active ingredient is formulated with a pharmaceutical excipient for topical administration.

13. The pharmaceutical composition of claim 12, containing at least one second active ingredient.

14. The pharmaceutical composition of claim 13, wherein said at least one second active ingredient is an antibiotic, antifungal, antibacterial or antiseptic agent.

15. The pharmaceutical composition of claim 14, wherein said at least one second active ingredient is selected from the group consisting of neomicine sulfate, bacitracin zinc and chlorhexidine gluconate.

16. A process for the preparation of the compounds of formula I' according to claim 7, comprising the steps of
(a) treating 3-protected estrone of formula II'

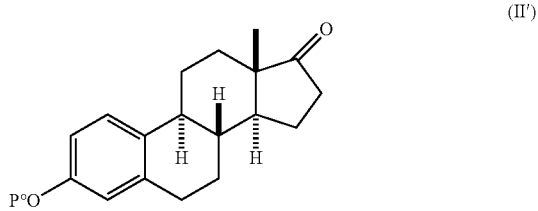

wherein P° is an alkali-stable protecting group, with an alkali metal 5-pentynol derivative of formula III'

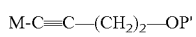

wherein M is an alkali metal and P' is an alkali-stable protecting group;

(b) subjecting the resulting compound of formula I″

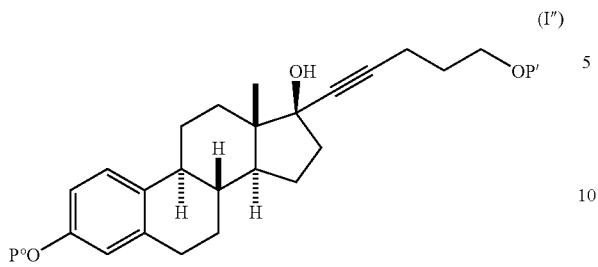
(I″)

wherein P° and P' are as defined above,
to total or partial deprotection and recovering a compound of formula I'a, I'b or I'c

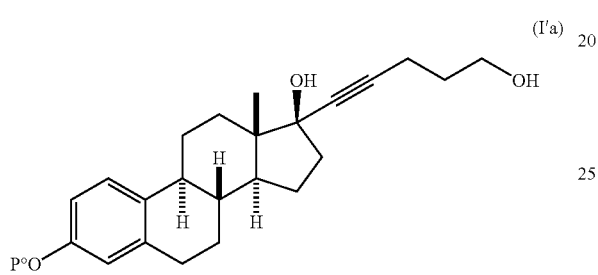
(I'a)

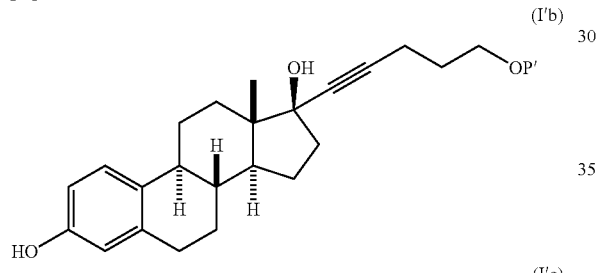
(I'b)

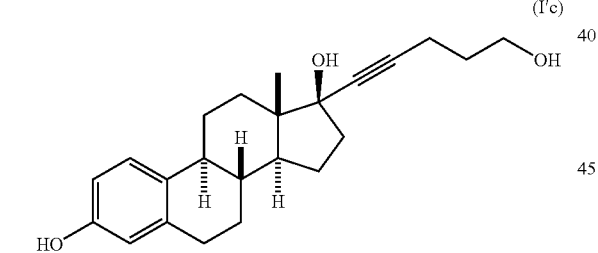
(I'c)

wherein P° and P' are as defined above;
(c) optionally treating the resulting compound of formula I'a, I'b or I'c with a reactive derivative of a lower alkanoyl acid Alk-OH, wherein Alk is lower alkanoyl, to obtain a compound of formula I'd, I'e or I'f

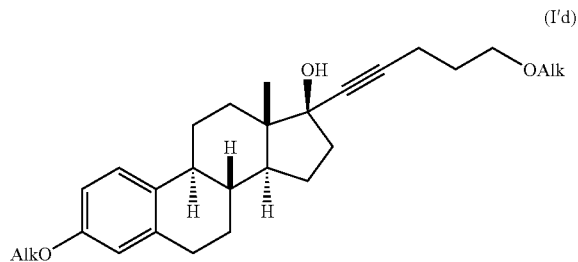
(I'd)

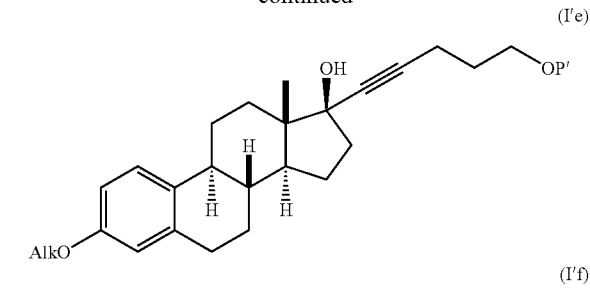
(I'e)

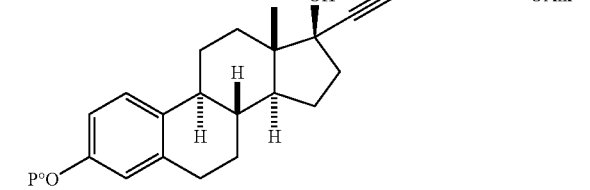
(I'f)

wherein P°, P' and Alk are as defined above;
(d) optionally removing the protecting group P° or P' from the compounds of formula I'e and I'f to obtain the compound of formula I'g or I'h

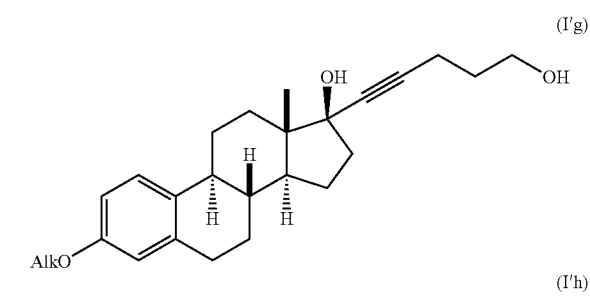
(I'g)

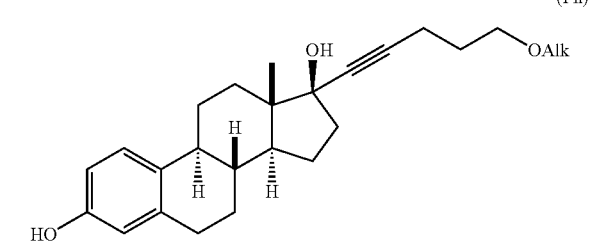
(I'h)

wherein Alk is as defined above; and
(e) optionally treating the resulting compound of formula I'g or I'h wherein Alk has the meaning defined above, with a reactive derivative of an alkanoic acid Alk'-OH to obtain an asymmetric diester of formula I'i or I'j

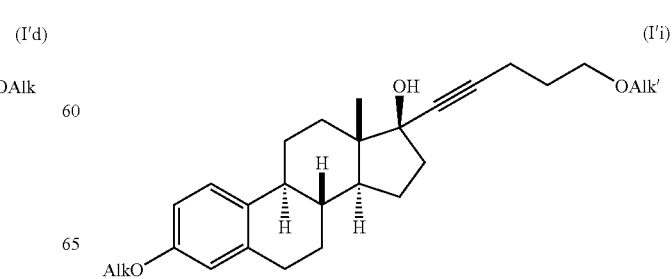
(I'i)

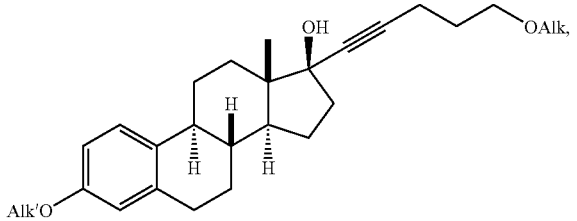

(I'j)

wherein Alk and Alk' are different lower alkanoyl groups.

17. The process of claim 16, wherein said alkali-stable protecting groups $P^o$ and $P'$ are selected from $Si(Alk)_3$ and 2-tetrahydropyranyl.

18. The process of claim 17, wherein each protecting group $P^o$ and $P'$ is 2-tetrahydropyranyl or t-butyldimethylsilyl.

19. The process of claim 16, wherein said $P^o$ group is 2-tetrahydropyranyl and said $P'$ group is t-butyldimethylsilyl.

* * * * *